United States Patent [19]

Cardenas et al.

[11] 4,168,271
[45] Sep. 18, 1979

[54] UNSATURATED VITAMIN E INTERMEDIATES—DEHYDRO AND DIDEHYDRO α-TOCOPHEROLS

[75] Inventors: Carlos G. Cardenas; Zia U. Din, both of Jacksonville, Fla.

[73] Assignee: SCM Corporation, New York, N.Y.

[21] Appl. No.: 832,419

[22] Filed: Sep. 12, 1977

Related U.S. Application Data

[63] Continuation-in-part of Ser. No. 786,973, Apr. 13, 1977, which is a continuation-in-part of Ser. No. 596,426, Jul. 16, 1975, abandoned.

[51] Int. Cl.² ............................................. C07D 311/70
[52] U.S. Cl. .............................. 260/345.5; 260/654 R; 585/600; 585/641
[58] Field of Search ....................................... 260/345.5

[56] References Cited

U.S. PATENT DOCUMENTS

| | | | |
|---|---|---|---|
| 3,346,595 | 10/1967 | Folkers et al. | 260/345.5 |
| 3,789,086 | 1/1974 | Frick et al. | 260/345.5 |
| 4,039,591 | 8/1977 | Close et al. | 260/345.5 |

*Primary Examiner*—Nicky Chan
*Attorney, Agent, or Firm*—A. Joseph Gibbons

[57] ABSTRACT

New dehydrotocopherols, namely cis- and trans- 3',4'-dehydrotocopherol; cis- and trans- 4',5'-dehydrotocopherol; and 4',4'-a-dehydrotocopherol, and new didehydrotocopherols, namely cis- and trans- 3',4'-11',12'-didehydrotocopherol; cis- and trans- 4',5'-11',12'-didehydrotocopherol; and 4',4'a-11',12'-didehydrotocopherol, are useful intermediates in the preparation of Vitamin E.

These intermediates are prepared by reacting trimethylhydroquinone under acid catalysis with certain $C_{20}$ intermediates, namely:

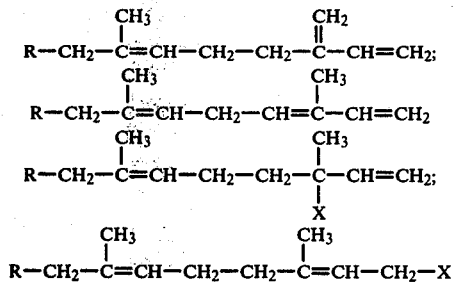

where R represnts a 3,7-dimethyloctyl or a 3,7-dimethyl-6-octenyl radical and X is halogen, hydroxyl, acetate, $C_{1-4}$ alkanoate, $C_{3-4}$ alkenoate, aralkenoate and benzoate.

8 Claims, No Drawings

UNSATURATED VITAMIN E INTERMEDIATES—DEHYDRO AND DIDEHYDRO α-TOCOPHEROLS

This is a continuation-in-part application of copending Application Ser. No. 786,973 filed Apr. 3, 1977 which in turn is a continuation-in-part of Application Ser. No. 596,426 filed July 16, 1975, now abandoned, all cases filed in the name of Carlos G. Cardenas and Zia Ud Din and assigned to the assignee of the present Application. Priority to Applications Ser. No. 786,973 and 596,426 is claimed and these cases are hereby incorporated by reference.

The present invention relates to the synthesis of new Vitamin E intermediates, namely,
(a) dehydrotocopherol isomers having a single ethylenic unsaturation at the 3',4'-position, the 4',5'-position or the 4',4'a-position;
(b) didehydrotocopherol isomers having two ethylenic unsaturations, i.e. the dehydrotocopherol shown in (a) with additional ethylenic unsaturation at the 11',12'-portion.

For purposes of identification and naming, the unsaturated α-tocopherol structures are shown generally as follows:

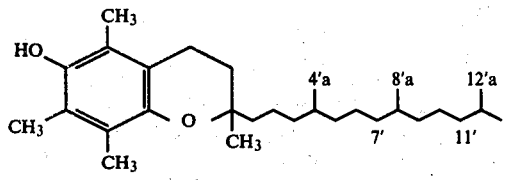

BACKGROUND OF THE INVENTION

The synthesis of Vitamin E, that is, α-tocopherol (5,7,8-trimethyltocol) in the past has been accomplished primarily by reacting trimethylhydroquinone (TMHQ) with iso-phytol (3,7,11,15-tetramethylhexadec-1-en-3-ol) in a condensation reaction with a catalyst.

The reaction is well known and has been practiced for many years. The related phytol (3,7,11,15-tetramethylhexadec-2-en-1-ol) has also been used in the reaction with trimethylhydroquinone and a catalyst to produce Vitamin E. A procedure with isophytol under relatively mild conditions to obtain a high yield was published in the *Journal of Organic Chemistry*, Vol. 36 (19), pp. 2910–12, Wehrli, Fryer & Metlesics.

The various routes to phytol and its isomers have been reviewed by Stalla-Bourdillon, *Ind. Chim. Belg.*, 35, 13 (1970). With few exceptions, these routes utilize a $C_{10}$ intermediate (natural or synthetic) and proceed to the $C_{20}$ phytol or isophytol by sequential addition of various carbon units ($C_3$ or less). The steps are numerous, and the syntheses are costly.

SUMMARY OF THE INVENTION

The present invention relates to:
1. A composition comprising a mixture of dehydro-α-tocopherol isomers consisting of cis- and trans-3',4'-dehydro-α-tocopherol; cis- and trans-4',5'-dehydro-α-tocopherol; and 4',4'a-dehydro-α-tocopherol.
2. A composition comprising a mixture of didehydro-α-tocopherol isomers consisting of cis- and trans-3',4'-11',12'-didehydro-α-tocopherol; cis- and trans-4',5'-11',12'-didehydro-α-tocopherol; and 4',4'a-11',12'-didehydro-α-tocopherol.

One aspect of the present invention is a process for preparing the dehydrotocopherol or didehydrotocopherol compounds shown in 1 and 2 above wherein trimethylhydroquinone is reacted with $C_{20}$ compounds having the formula selected from the group consisting of

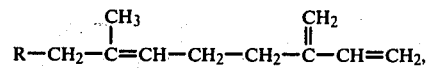

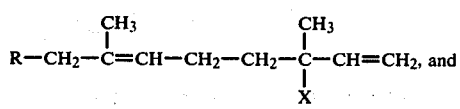

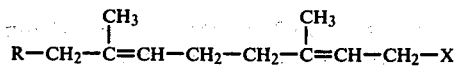

wherein R represents a 3,7-dimethyloctyl or a 3,7-dimethyl-6-octenyl radical and X is halogen, hydroxyl, $C_{1-4}$ alkanoate, $C_{3-4}$ alkenoate, aralkenoate and benzoate, or lower alkoxide substituents.

Another aspect of the present invention is a process for preparing di-α-tocopherol (Vitamin E) which comprises:
(a) reacting under acid catalysis trimethylhydroquinone and $C_{20}$ compounds having the formula selected from the group consisting of

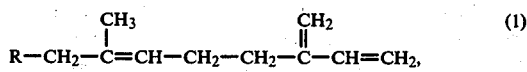

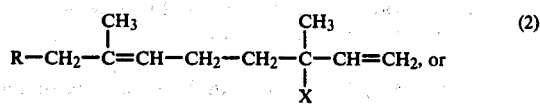

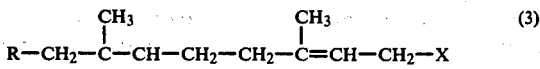

wherein R represents a 3,7-dimethyloctyl or a 3,7-dimethyl-6-octenyl radical and X is halogen, hydroxyl, alkanoate or alkoxide substituents to yield one or more of the isomeric dehydro-α-tocopherols or didehydro-α-tocopherols illustrated in 1 and 2 above.
(b) hydrogenating the olefinic unsaturation of the various unsaturated tocopherols produced in (a) above with hydrogen and a hydrogenation catalyst in the presence of a solvent;
(c) isolating di-α-tocopherol therefrom.

DETAILED DESCRIPTION

The present invention relates to new Vitamin E intermediates namely dehydro-α-tocopherols and didehydro-α-tocopherols. The dehydrotocopherols include cis- and trans-3',4'-dehydro-α-tocopherol; cis- and trans-4',5'-dehydro-α-tocopherol; 4',4'a-dehydro-α-tocopherol and isomeric mixtures. The dehydrotocopherols include cis- and trans-3',4'-11',12'-didehydro-α-tocopherol; cis- and trans-4',5'-11',12'-didehydro-α-tocopherol; 4',4'a-11',12'-didehydro-α-tocopherol and isomeric mixtures thereof.

The dehydro and didehydro-α-tocopherols can be prepared by reacting trimethylhydroquinone under acid catalysis with certain $C_{20}$ intermediates exemplified by the following structures:

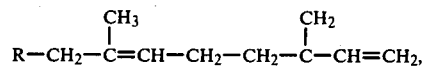   A.

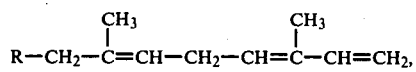   A-1.

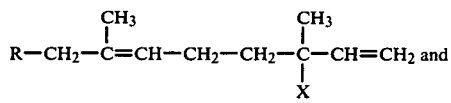   B.

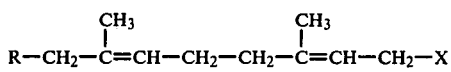   C.

where R represents a 3,7-dimethyloctyl or a 3,7-dimethyl-6-octenyl radical and X is halogen, hydroxyl, alkoxide, $C_{1-4}$ alkanoate, $C_{1-4}$ alkenoate, aralkenoate or benzoate. For purposes of this invention the compound designated as A above will be understood to include either structure A or its 1,4-diene counterpart illustrated as A-1 above.

Preparation of $C_{20}$ Trienes and $C_{20}$ Tetraenes

The above indicated prepared $C_{20}$ triene and tetraene compounds are conveniently prepared according to procedures shown in Applications Ser. No. 786,973 and 596,426 to which priority is claimed and which are incorporated herein by reference. In the parent cases it was shown that an acyclic terpene derivative of the 2,6-dimethyloctane series having a reactive allylic halide group can be readily coupled with a second $C_{10}$ aliphatic compound having a terminal halogen atom to produce a $C_{20}$ triene, sometimes hereinafter referred to as phytatrienes as for example:

D. 3-methylene-7,11,15-trimethyl-1,6-hexadecadiene, or
E. 3,7,11,15-tetramethyl-1,3,6-hexadecatriene.

Compound D can be obtained by coupling chloromyrcene (see specific examples for preparation of 3-chloro-6-methylene-2-methyloctadiene-1,7 from β-myrcene) with the Grignard reagent prepared from 3,7-dimethyloctylchloride as illustrated by the following equation:

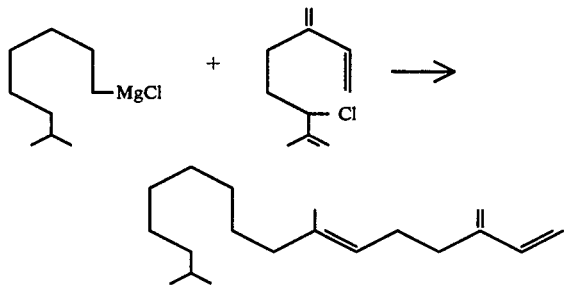

The Grignard coupling reaction occurs with allylic rearrangement (double bond migration) to produce a $C_{20}$ compound having generally the same skeleton as phytol.

Preferably the reaction is carried out by first preparing the Grignard of the dimethyloctyl chloride and then reacting the Grignard with chloromyrcene. The reaction also is preferably carried out in the presence of a dipolar aprotic solvent and a cuprous or cupric compound or other copper or iron catalyst compound, such as cuprous chloride, cupric chloride, lithium tetrachlorocuprate ($Li_2CuCl_4$), or ferric chloride, these salts giving a high degree of the selectivity for displacement with allylic rearrangement described above. It is also a preferred aspect of the invention that the coupling reaction is carried out in the sequence of slow addition of the Grignard to the chloromyrcene. The catalyst may be added to either the Grignard or the Grignard reagent or to the allylic halide and carrying out the reaction in a homogeneous catalytic reaction by the sequence of addition of the Grignard reagent to the allylic halide.

This coupling has been successfully practiced with a number of allylic halides, and the present invention is not limited to a particular allylic halide or class of halides. Other unsaturated terpene hydrocarbons which can be halogenated and then coupled with a Grignard are alpha-myrcene (6-methylene-2-methylocta-1,7-diene); beta-ocimene (3,7-dimethylocta-1,3,6-triene); alpha-ocimene (3,7-dimethylocta-1,3,7-triene); and citronellene (3,7-dimethylocta-1,6-diene).

$C_{20}$ tetraenes result when the Grignard reagent used in the above sequence is 3,7-dimethyloct-6-enyl Grignard. The resultant $C_{20}$ products are sometimes herein referred to as phytatetraenes as for example:

F. 3-methylene-7,11,15-trimethyl-1,6,14-hexadecatriene, or
G. 3,7,11,15-tetramethyl-1,3,6,14-hexadecatetraene.

Compound F is prepared by reacting chloromyrcene with 3,7-dimethyloct-6-enyl Grignard in the same manner as indicated for Compound D above. This Grignard may be prepared directly from citronellyl chloride (3,7-dimethyl-6-octenyl chloride) or by a Grignard exchange of 3,7-dimethyloctadiene-1,6 with propyl magnesium chloride as described in Example 3.

Dehydrotocopherols and didehydrotocopherols can be prepared directly from the above described $C_{20}$ trienes and/or $C_{20}$ tetraenes. Alternatively these phytatrienes and phytatetraenes may be converted to the corresponding unsaturated phytols, or unsaturated phytyl halides, $C_{1-4}$ alkanoates, $C_{3-4}$ alkenoates, benzoates each of which may separately be reacted with trimethylhydroquinone to yield dehydrotocopherols and didehydrotocopherols.

Synthesis of Dehydrotocopherols

It has been found that when trimethylhydroquinone is reacted under acid catalysis under controlled conditions with certain $C_{20}$ intermediates having the following formulas:

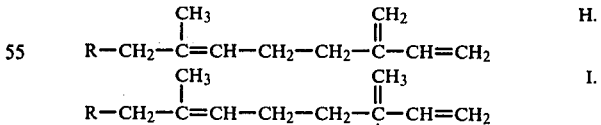   H.

I.

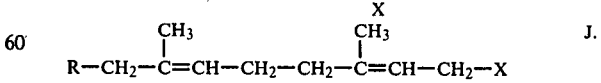   J.

where R is the 2,6-dimethyloctyl radical and X is selected from the group consisting of halogen (chlorine, bromine), hydroxide, lower alkoxide, acetate, and other derivatives, that isomeric mixtures of dehydrotocopherols result. Such dehydrotocopherol isomeric mixtures consist of:

K. cis-trans-3',4'-dehydrotocopherol
L. cis-trans-4',5'-dehydrotocopherol, and
M. 4'4'a-dehydrotocopherol The composition of the isomeric mixtures (ratio of a:b:c) vary with the starting material, the acid catalyst, reaction temperature reaction solvent and order of addition of reactants. The five isomers are resolved into three peaks using gas chromatography as exemplified in Example 14. Hydrogenation of these isomers yield authentic d,l,-α-tocopherol. When the reaction conditions are too severe or the acid catalyst too strong additional peaks appear in the gas chromatogram indicative of further ring formation resulting from the additional ethylenic unsaturation. Conditions must be controlled to avoid further cyclization and resinification.

VPC data were obtained for the dehydrotocopherols and the Vitamin E products on a gas chromotograph Apiezon N packed column programmed at 150° to 285° at 6°/min.

Characterization of the dehydro-α-tocopherols was accomplished by NMR and by conversion (hydrogenation) to α-tocopherol and comparison of its NMR spectrum with that of an authentic sample as follows:

The dehydro-α-tocopherols were characterized by analysis of the 60 and 250 MHz NMR spectra of the mixture and of fractions obtained by preparative gas chromatography. Significant signals in the spectrum of the mixture and their assignments are as follows:

| | | |
|---|---|---|
| 4.1δ | broad singlet | hydroxyl |
| 2.4–2.7δ | triplet J~7Hz | benzyl CH$_2$ |
| 2.1–2.2δ | singlets | aryl CH$_3$ |
| 1.1–1.3δ | singlets | chroman CH$_3$ |
| 0.7–1.0δ | singlets | other CH$_3$ |

Additionally, a triplet centered at ~5.1δ is assigned to the vinyl proton in the 3',4'- and the 4',5'-isomers, while the vinyl protons of the 4',4'aisomer appear as a broad singlet at 4.6δ. The vinyl methyls of the cis-isomers are seen at 1.66 and 1.67δ, whereas those of the trans-isomers appear at 1.55 and 1.58δ.

Synthesis of Didehydrotocopherols

A further aspect of the invention relates to the synthesis of certain didehydrotocopherols. If trimethylhydroquinone is reacted under acid catalysis with C$_{20}$ intermediates having additional unsaturation as shown in the following formulas,

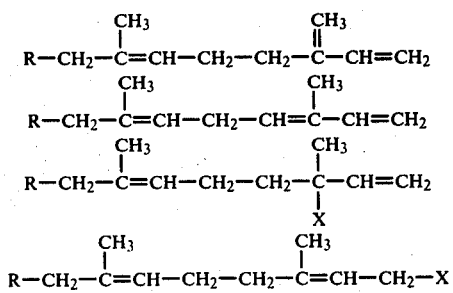

including their geometrical isomers, where R is the 3,7-dimethyl--6-octenyl radical and X is selected from the group consisting of halogen (chlorine,bromine),hydroxide, lower alkoxide, and ester functionality such as acetates, then isomeric mixtures of didehydrotocopherols will be produced. Such didehydrotocopherols isomeric mixtures consist of:

R. cis- and trans- 3',4'-11',12'-didehydrotocopherol;
S. cis- and trans- 4',5'-11',12'-didehydrotocopherol; and
T. 4',4'a-11',12'-didehydrotocopherol.

The synthesis of these compounds from trimethylhydroquinone will be similar to that of the dehydrotocopherols discussed above but the choice of solvents, catalysts, and reaction conditions (temperature, time) will be somewhat more critical due to the presence of the additional double bond at the 11',12' position. For highest conversions and purity, Lewis acid catalysts such as BF$_3$ etherate, zinc chloride, and aluminum chloride (with or without added aluminum powder) are used in conjunction with mixed solvents such as benzene/ethylacetate under reflux conditions or at temperatures of the order of 30°–90° C. and preferably 30°–60° C. Isolation of the didehydrotocopherols and conversion to Vitamin E will parallel the work-up suggested for the dehydroanalogs. Conversion and purity of product may be followed by gas chromatography, N.M.R., infrared spectra, and elemental analysis as well as similar characterization of the dl-α-tocopherols formed by catalytic hydrogenation of the intermediate mixtures.

The following examples demonostrate the importance of the parameters discussed above. Purity of the products was determined by N.M.R., gas chromatography and by hydrogenating a portion of the product in acetic acid (glacial) using 5% Pd on BaSO$_4$ catalyst at approximately 55 lbs./in.$^2$ for four hours and analyzed by comparison with values for standard Vitamin E.

Experimental Procedure

As a general procedure tetramethylhydroquinone (TMHQ) is dissolved in a suitable solvent containing acid catalyst and heated to reflux under nitrogen. Then, the C$_{20}$ intermediate or its derivative is introduced slowly from an additional funnel over a 2-hour period. The reaction mixture is refluxed for a specified period of time to effect a good conversion. At the end of the reaction, it is important to remove unconsumed TMHQ from the product because the ratio of vinyl to phenolic protons in the NMR analysis determines the purity of the product. Accordingly, the reaction mixture is dissolved in pentane and washed several times with 78% aqueous methanol. Unless otherwise defined the term dehydrophytol means 6,7-dehydrophytol. Temperatures are given in degrees Centigrade unless otherwise indicated.

A portion of each reaction dehydrotocopherol was hydrogenated in glacial acetic acid using 5% Pd on BaSO$_4$ catalyst to give dl-α-tocopherol. A few typical examples are described here in the case of dehydrophytol; however, the same experimental procedures are applicable to dehydrophytyl acetate, dehydrophytyl chloride, phytatriene, and phytatraene. These compounds were analyzed by VPC (Apiezon N, Column B, 150°, 285°, 6°/min.), N.M.R., and L.C.

EXAMPLE 1

Preparation of 3-chloro-6-methylene-2-methyloctadiene-1,7

Chloromyrcene was prepared by placing sodium carbonate (200 grams) in a flask with 505.2 grams of beta-pinene pyrolysate which analyzed at 80.9% beta-myrcene (408.7 grams, 3.00 moles). The reactor was flushed with nitrogen and then, while stirring in the dark at 25°±2° C., chlorine (160.4 grams, 2.3 moles) was added via a fritted glass tube over a 220-minute period. Stirring was continued for thirty minutes after completion of addition at which time the solids were removed by filtration providing 584.7 grams of crude chloromyrcene. Gas chromotographic analysis without an internal tandard indicated 70.3% conversion of beta-myrcene and 89.7% theory yield of 3-chloro-6-methylene-2-methyloctal,7-diene(chloromyrcene).

EXAMPLE 2

Preparation of 3-methylene-7,11,15-trimethylhexadeca-1,6,14-triene

A mixture consisting of 2.5 g (0.104 mole) magnesium, 18.4 g (0.1 mole) of 95% citronellyl chloride, 100 mls. of tetrahydrofuran and one drop of dibromomethane was refluxed for 2 hours to give citronellyl magnesium chloride in almost quantitative yield.

In a 500-mil., three-neck flask equiped with a mechanical stirrer, thermometer and an addition funnel were placed 18.3 g (0.1 mole) of 95% chloromyrcene, 100 mls. of tetrahydrofuran, and 0.1 g of cuprous chloride. The mixture was stirred and cooled to −7°. Then the above prepared Grignard was added dropwise during a 2-hour period and the reaction temperature was maintained at −7° during the addition. Upon completion of addition, the reaction mixture was quenched with diluted hydrochloric acid (2%) at 0° and worked up using pentane solvent. The combined organic portion was filtered through magnesium sulfate and the solvent evaporated in a rotary evaporator to give 32.5 g of product containing 46% of the $C_{20}$ tetraene, thus a 54.6% theory yield. The selectivity for displacement with allylic rearrangement was 96.3%.

In analogous fashion, 3,7-dimethyloctyl chloride provides 3,7-dimethyloctylmagnesium chloride which is coupled with chloromyreene to give the $C_{20}$ triene 3-methylene-7,11,15-trimethyl-1,6-hexadecadiene in 68% yield and with 99% selectivity.

EXAMPLE 3

Preparation of Citronellyl Magnesium Chloride via Grignard Exchange

In a one-liter, three-neck flask equipped with an addition funnel, thermometer, stirrer and condenser were placed 7.2 g (0.3 mole) of magnesium, 300 mls. of ether and 23.6 g (0.3 mole) of n-propyl chloride. The reaction mixture was stirred gently and refluxed for 3 hours. At the end of that period almost all the magnesium had reacted to give n-propyl magnesium chloride.

The reaction mixture was stirred vigorously and cooled at 0°. Then 38.3 g (0.25 mole) of 90% 3,7-dimethyl-1,6-octadiene was added at 0° during 10 minutes. Dicyclopentadienyltitanium dichloride (3.5 g) was then added in one portion at −2° and an exothermic reaction was observed. The reaction mixture was allowed to come to room temperature slowly and then refluxed. After 18 hours, 77% of the 3,7-dimethyl-1,6-octadiene had been converted to citronellyl magnesium chloride.

EXAMPLE 4

3′,4′-dehydrotocopherol by Condensation between TMHQ and 6,7-dehydrophytol (3,7,11,15-tetramethylhexadeca-2,6-dien-1-ol) Using Boron Trifluoride Etherate in Ethyl acetate Into a 100 ml. 3-neck round bottomed flask flamed under $N_2$, were placed 2 gm (0.013 mole) of TMHQ and 0.1 gm of Al powder and a steady flow of $N_2$ was maintained. Then a solution of 1 ml. of $BF_3$ etherate in 35 mil ethyl acetate was added and the mixture stirred and heated to a gentle reflux. Through an addition funnel 2 gm (0.0068 mole) of 6,7-dehydrophytol in 2 mil of ethyl acetate was introduced slowly over a 1-hour period, and the reaction mixture refluxed for 5 hours. It was allowed to cool under $N_2$ and then 20 ml of 5% sodium carbonate solution was added. The aqueous portion was separated and extracted once with pentane. From the combined organic portion the solvent was removed in a rotary evaporator at 70°. The semi-solid residue containing unreacted TMHQ was dissolved in pentane and washed four times with 15 ml of 78% aqueous methanol. Each methanol wash was extracted once with pentane. The combined pentane solution of the product was finally washed once with sodium chloride solution and filtered through anhydrous $MgSO_4$. The solvent was stripped in a rotary evaporator to give 2.9 gm of a yellow syrup containing the crude 3′,-4′ dehydrotocopherol. Good quality dehydrotocopherol isomers of 75–80% purity was obtained. NMR indicated a ratio of vinyl to phenolic protons of 0.87:1.

Hydrogenation of Dehydrotocopherol

Approximately 0.5 gm of crude dehydrotocopherol was dissolved in 40 ml glacial acetic acid and 0.5 gm of the catalyst (5% Pd on $BaSO_4$) was added. The mixture was hydrogenated in a Parr shaker at 55 lbs/in$^2$ for 4 hours. After filtration the solvent was removed in a rotary evaporator at 85° C. The residue was dissolved in 20 ml pentane and washed once with 5% $Na_2Co_3$ solution and filtered through anhydrous $MgSO_4$. Pentane was removed in the evaporator to give 0.4 gm dl-α-tocopherol as a yellow syrup. VPC analysis showed a single peak.

EXAMPLE 5

Example 4 was repeated using different catalysts, solvent or solvent mixtures and reaction conditions (temperature, time).

The importance of aluminum powder and the nature of the reaction solvent was shown by performing a similar reaction without any aluminum powder and substituting benzene for the ethyl acetate. In this case, the purity of the tocopherol decreased to 65%.

When the reaction was performed in dioxane, a relatively polar solvent, no condensation resulted from stirring at room temperature over a 16-hour period. However, when the reaction mixture was refluxed for 3 hours a semi-solid product was obtained which showed several new peaks in the VPC for undesired by-products not fully characterized.

Repeating the experiment and changing the solvent to a 1:1 mixture by volume of benzene/ethyl acetate showed no condensation took place at room temperature. When the mixture was refluxed for 3 hours a satisfactory yield of dl-α-tocopherol of 70% purity was obtained after hydrogenation.

Repeating the experiment in ethyl acetate and refluxing for 3 hours gave the usual three VPC peaks corresponding to the isomeric dehydrotocopherols. Hydrogenation gave 77% pure tocopherol.

$BF_3$/TMHQ Complex

Into a 100 ml 3-neck round bottomed flask flamed under $N_2$ were placed 4.6 gm (0.03 mole) of TMHQ, 25 ml. $CH_2Cl_2$ and 2 ml. nitromethane and the mixture cooled to 20°. The suspension formed was stirred and $BF_3$ gas was introduced slowly. At the beginning, the color of the reaction mixture turned green, the suspension became thinner and after 10 minutes 2.1 gm (0.03 mole) of $BF_3$ had been consumed by the reaction mixture. The saturation point was noted by thick white smoke escaping from the drying tube. After stirring another 20 minutes, the reaction mixture was cooled to $-20°$, and 10 gm (0.0338 mole) of dehydrophytol was slowly added through an addition funnel keeping the temperature at $-20°$ over 1.5-hour period. The reaction mixture was stirred for a further 1.5-hour period, allowed to come to room temperature and killed with water. The organic portion was washed once with water and the combined water portion in turn was extracted once with $CH_2Cl_2$. The solvent was removed in the rotary evaporator and worked up as described previously to give 11.1 gm of a brown syrup containing crude dehydrotocopherol. The VPC analysis showed the presence of dehydrotocopherol in not more than 20% theory yield.

EXAMPLE 6

Zinc Chloride Catalyst in Ethyl Acetate/Toluene

The reaction between TMHQ and 6,7-dehydrophytol was first carried out using the combined acid catalyst ($ZnCl_2$/$NaHSO_4$) in benzene.

Into a 100 ml round bottomed 3-neck flask fitted with a condenser, stirrer, Dean-Stark distillation receiver, addition funnel and thermometer were placed 1 gm of powdered $NAHSO_4$, 2 gm of powdered $ZnCl_2$, 6.3 gm (0.041 mole) of TMHQ and 50 ml benzene. The mixture was heated to reflux and 25 ml of benzene was collected in the Dean-Stark trap. Then 5.1 gm (0.016 mole) of dehydrotophytol was added slowly into the boiling reaction mixture over a 2-hour period. The reaction mixture was refluxed for 2 hours and worked up as described previously to give 5.9 gm of product, as mixture of dehydrotocopherol and other by-products. In this case the ratio of vinyl to phenolic protons in the product was 0.41:1. For a pure sample of dehydrotocophenol this ratio should be 1:1. Accordingly, VPC analysis of the hydrogenated product showed a peak for tocopherol and a shoulder for the impurity. Similar unsatisfactory results were obtained when the reaction was carried out in toluene.

The reaction using only zinc chloride and a mixed solvent system (ethyl acetate/toluene) proved to be a preferred system.

The addition of dehydrophytol into a boiling mixture consisting of TMHQ, zinc chloride, ethyl acetate and toluene was followed by a reflux period of 3 hours. After workup and hydrogenation, dl-α-tocopherol of 75% purity was obtained. VPC analysis showed no by-product impurity peak (no tocopherol shoulder peak).

EXAMPLE 7

Powdered Aluminum Chloride in Benzene/Ethyl Acetate

Into a 100 ml round bottomed 3-neck flask flamed under $N_2$ were placed 1.2 gm (7.8 m-mole) of TMHQ, 30 ml of 1:1 benzene/ethyl acetate and 2 gm (6.8 m-mole) of 6,7-dehydrophytol. The reaction mixture was stirred and heated slowly to reflux under $N_2$. Then 1.0 gm of anhydrous $AlCl_3$ powder was added in small portions over 30 minutes and the reaction mixture refluxed for 3 hours. It was allowed to come to room temperature and quenched with water. The usual workup as described above gave 2.8 gm of crude dehydrotocopherol. The product showed the three usual peaks A, B, and C for the dehydrotocopherol isomers. Peaks A and B are in greater proportion than peak C. Hydrogentation gave good quality dl-α-tocopherol of 75–80% purity as verified by VPC, NMR and LC analysis.

Repetition of this experiment using ethyl acetate as the solvent in place of the mixture gave a product consisting of one major peak B with relatively small amounts of A and C. After hydrogenation, dl-α-tocopherol VPC showed a peak having a shoulder component believed to represent a tricyclic impurity.

Repetition of this experiment using only benzene in place of the solvent mixture afforded a low purity tocopherol. The conclusion reached is that a mixed solvent of benzene/ethyl acetate is superior to either component used alone.

When the reaction was conducted by incremental addition of $AlCl_3$ powder to a refluxing mixture of 6,7-dehydrophytol and TMHQ in 1:1 benzene/ethyl acetate solvent followed by the usual hydrogenation, tocopherol of 80% purity was obtained. By following the reaction by VPC analysis (Apiezon N, 150°–185°, 6°/min. alt 32) it was seen that the dehydrophytol was consumed within a 2-hr. reflux period.

EXAMPLE 8

Sulfuric Acid or Methane-Sulfonic Acid in Ethyl Acetate

The condensation of TMHQ with 6,7-dehydrophytol was conducted in ethyl acetate using concentrated sulfuric acid as catalyst.

Into a 100 ml 3-neck round bottomed flask flamed under $N_2$ were placed 1 gm (6.58 m-mole) of TMHQ, 5 ml of ethyl acetate and 0.2 ml of concentrated sulfuric acid. The reaction mixture was stirred at room temperature while 2 gm (6.79m-mole) of dehydrophytol was added slowly over a 10-minute period keeping the temperature at 30°. The reaction mixture was stirred at room temperature for 2 hours and at 60° C. for an additional hour, and worked up as described previously to yield 2.5 gm of crude isomeric dehydrotocopherols. A theoretical yield of 50% tocopherol at 64% purity was obtained.

EXAMPLE 9

Preparation of cis- and trans-3'-4'-dehydro-α-tocopherol from Phytatriene

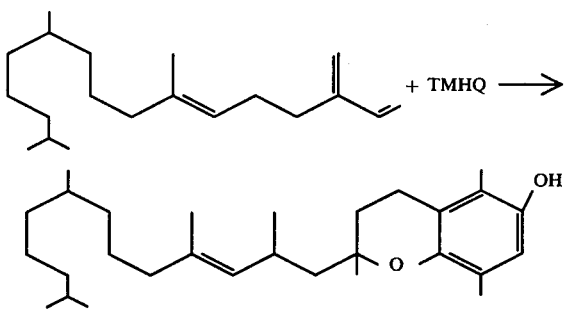

The overall theory yield of the reaction sequence in the preparation of dehydrophytol from phytatriene is 75% and there are numerous chemicals consumed in the process. Therefore, economically it would be a great advantage to condense TMHQ with phytatriene to give 3'-4'-dehydrotocopherol and its isomers. Various syntheses starting with phytatriene are set forth below. Phytatriene is more specifically defined as 3,7,11,15-tetramethylhexadeca-1,3,6-triene or its isomeric counterparts, i.e., 3-methylene-7,11,15-trimethylhexadeca-1,6-diene.

Indeed, phytatriene does react with TMHQ in the presence of AlCl₃ to form 3'-4'-dehydrotocopherol and its isomers which after the usual hydrogenation give dl-α-tocopherol. It was thought that Cu⁺ would complex with the 1,3-diene system in the phytatriene and a more selective alkylation of TMHQ would result. Therefore, in a few reactions Cu⁺ was employed. In each case the crude reaction product was hydrogenated as described previously.

When a suspension of cuprous chloride in phytatriene was added into a boiling mixture of TMHQ and AlCl₃ in ethyl acetate/benzene, a rapid reaction took place and the usual follow-up gave tocopherol of 55% purity.

In a better procedure a mixture of TMHQ, phytatriene and powdered cuprous chloride in ethyl acetate/benzene was stirred and heated to reflux while powdered AlCl₃ was added in small portions. A mixture consisting of 1.0 gm (6.6 m-moles) of TMHQ, 30 ml of 1:1 benzene/ethyl acetate, 0.2 gm of cuprous chloride and 2 gm (7.2 m moles) of phytatriene was stirred and heated to reflux under nitrogen. Then 0.4 gm of anhydrous aluminum chloride powder was added in small portions over 10 minutes and the reaction mixture refluxed for an additional 5-hour period. After the usual workup and the hydrogenation of the crude product as described, 2.3 gm of the product containing 64.0% tocopherol was obtained (47.2% theory yield).

A triphenylphosphine-cuprous iodide complex was prepared in excellent yield by reluxing the two components in benzene for 8 hours. This complex was sparingly soluble in either benzene or ethyl acetate, the regular solvents for the condensation reaction. The reaction between TMHQ and phytatriene in the presence of this complex was carried out and dl-α-tocopherol of 70% purity was obtained after hydrogenation.

When phytatetraene is used in place of phytatriene in the above reaction corresponding yields of didehydrotocopherols of equal purity will be obtained.

EXAMPLE 10

6,7-dehydrophytyl chloride (3,7,11,15-tetramethyl-2,6-hexadecadienyl chloride); 6,7-dehydrophyl acetate and 6,7-dehydrophytol

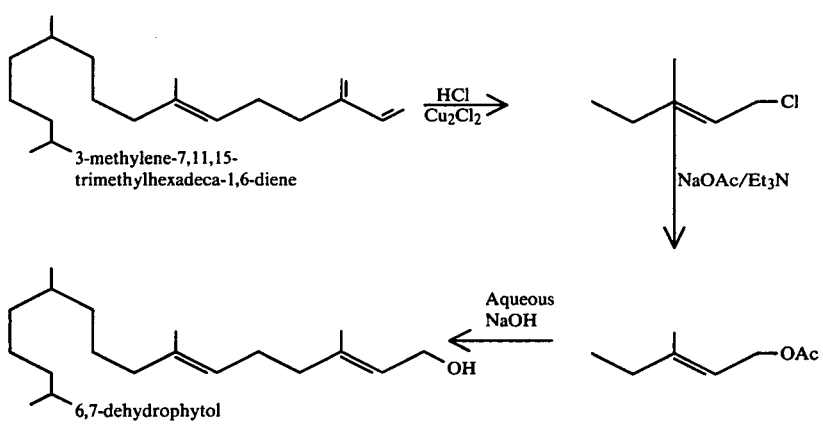

Conversion of phytatriene (3-methylene-7,11,15-trimethylhexadeca-1,6-diene) to 6,7-dehydrophytyl chloride can be accomplished by hydrochlorinating with Cu₂Cl₂ and HCl according to the procedure of U.S. Pat. No. 3,016,408.

In a specific example, 86.2 grams (0.312 mole) of the triene is added to a suitable vessel along with 0.8 gram of cuprous chloride (CU₂Cl₂), and the mixture is stirred and cooled to about −3°. Dry hydrogen chloride is then passed slowly into the mixture so that all of the gas is consumed and none escapes. The reaction is conducted slowly, over a few hours period with the addition of 11.7 grams (0.32 mole) of the hydrogen chloride. The mixture is then further stirred for 2 hours at about −3° and kept cold overnight, to produce 98.7 grams of 6,7-dehydrophytylchloride.

The 6,7-dehydrophytyl chloride can be reacted directly with trimethylhydroquinone to give 3',4'-dehydro-α-tocopherol and isomers or it can be further derivatized by known methods to give the corresponding alkanoates, alkenoates, benzoates, alkoxides as for example 3,7,14,15-tetramethyl-2,6-hexadecadienyl acetate. These intermediates may separately be reacted with trimethylhydroquinone to give the dehydrotocopherols or alternatively they may be converted to 6,7-dehydrophytol and isomers thereof.

Sodium acetate powder (68.4 grams) is then added to the 6,7-dehydrophytyl chloride (98.7 grams) plus 21.9 grams of sodium carbonate, and 170 ml of 1:1 DMF/benzene and 2.6 grams of tetrabutylammonium chloride. The mixture is mechanically stirred and heated to 102°–105° C. and kept at that temperature for 4 hours under nitrogen. The product is cooled and worked up with pentane, yielding 107.2 grams of 6,7-dehydrophytyl acetate The acetate of the above step (100 grams), 317 grams of 50% sodium hydroxide, and 0.3 grams of Aliquat 336 catalyst (a quaternary ammonium compound, Trademark General Mills) are then heated to reflux under nitrogen. The temperature of the mixture is about 115°, and the mixture is refluxed for about 2.0 hours and cooled under nitrogen. Eighty-six (86) grams of 6,7-dehydrophytol are obtained giving a theoretical yield of about 74.6% based on phytatriene. It is understood that the term dehydrophytol includes dehydroisophytol which is present in the product in the ratio of about 1:10 based on the amount of its isomer in the product. These two compounds give the same product when condensed with TMHQ.

The use of phytatetraenes as for example, 3-methylene-7,11,15-trimethylhexadeca-1,6,14-triene, in the same manner will produce 6–7,14–15 didehydrophytyl-chloride, alkoxides, acetates, all of which can be further reacted with TMHQ to yield the corresponding 3'–4',1-1'–12'-didehydro-α-tocopherols and isomers thereof, all of which will be converted to Vitamin E on hydrogenation.

EXAMPLE 11 dl-α-Tocopherol from 6,7-Dehydrophytyl Chloride

Both BF$_3$ etherate and AlCl$_3$ were employed in the condensation between TMHQ and dehydrophytyl chloride. The dehydrophytyl chloride used was that prepared in Example 10 above without further purification.

When the hydrochloride was added slowly into a boiling mixture containing TMHQ, BF$_3$ etherate and Al powder in ethyl acetate, no significant conversion was observed. However, after 6 hours at reflux the usual work-up gave a poor yield of isomeric dehydrotocopherols. This product after hydrogenation afforded tocopherol of 65% purity.

On the other hand, if the reaction is carried out in the presence of AlCl$_3$ in a mixture of ethyl acetate/benzene at reflux temperature, an excellent conversion was seen within one hour, but the dl-α-tocopherol obtained after hydrogenation showed a small shoulder in the VPC analysis.

EXAMPLE 12 dl-α-Tocopherol from 6,7-Dehydrophytyl Acetate

The condensation reaction between purified dehydrophytyl acetate and TMHQ in ethyl acetate using BF$_3$ etherate and Al powder was carried out at reflux temperature and worked up as described previously. The VPC patterns of the isomeric dehydrotocopherols and tocopherol were similar to those obtained from dehydrophytol.

EXAMPLE 13

Repetition of the reactions shown in Examples 1 through 12 above, wherein the C$_{20}$ intermediates exemplified as formulas N, O, P and Q above are used in place of the C$_{20}$ compounds exemplified by formulas H, I and J, will produce a mixture of didehydrotocopherols comprising cis- and trans-3',4'-11',12'-didehydrotocopherol; cis- and trans-4',5'-11',12'-didehydrotocopherol; and 4',4'a-11',12'-didehydrotocopherol. Preferred solvents are ethyl acetate and ethyl acetate/benzene (1:1 by volume) mixtures. Preferred catalysts are BF$_3$ etherate, aluminum chloride and mixtures additionally containing aluminum powder. Preferred reaction times are 1.5 to 3 hours at reaction temperatures of 30°–65° C. The didehydrotocopherols are readily converted to α-tocopherol by hydrogenation.

EXAMPLE 14

Isolation and Analysis of Dehydro-α-Tocopherols

Gas Chromatographic analysis of the dehydro-α-tocopherols was done on a Varian 2100 Instrument with a flame ionization detector and using a 1 meter×2.3 mm ID glass column packed with 10% Apiezon N on Anakrom ABS 90/100 mesh.

Routine analyses were run isothermally at 285°, but programming from 150° to 285° at 6°/minute was necessary in order to clearly see both starting materials and products. A 1 m×10 mm ID glass column with similar packing was employed for preparative separations.

The gas chromatogram of crude dehydro-α-tocopherols typically consists of 3 main peaks, A, B, and C. Hydrogenation followed by GC analysis under the same conditions showed that A, B, and C were consumed and a single major peak was formed eluting very close to B and identical with authentic α-tocopherol.

Peaks A, B, and C were isolated by preparative GC and were analyzed by 60 MHz and by 250 MHz NMR. All chemical shift values are taken from the 250 MHz spectra.

Careful examination of the 250 MHz spectra confirmed that A, B, and C are isomers with the α-tocopherol skeleton. The acid conditions required for the TMHQ condensation evidently isomerize the double bond giving rise to the following isomers:

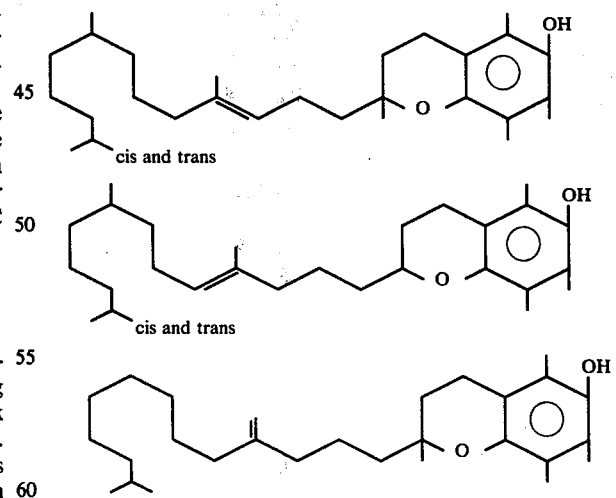

Distinguishing between these isomers was done mainly by taking note of the different chemical shifts of the vinyl methyls.

Peak A: The vinyl methyl at 1.66 and 1.67δ suggests the cis-isomers showing vinyl splitting. The assignments (which are virtually identical in all three spectra) are as follows:

| | | |
|---|---|---|
| 5.12δ | triplet J 6.5 Hz | Vinyl H |
| 4.16δ | singlet | Hydroxyl |
| 2.61δ | triplet J 7.0 Hz | Benzyl $CH_2$ |
| 2.11 and 2.16δ | singlets | Aryl $CH_3$ |
| 1.79δ | mult., 8 lines | Non-benzyl $CH_2$ on chroman |
| 1.98δ | distorted triplet | Allylic H |
| 1.66–1.67δ | several singlets | Vinyl $CH_3$ |
| 1.22, 1.25, and 1.26δ | three singlets | $CH_3$ on chroman |

Peak A is identified as containing cis-3',4',dehydro-α-tocopherol and cis-4',5'-dehydro-α-tocopherol.

Peak B: The main component of this peak appears to be one of the trans isomers as shown by the vinyl methyl signal at 1.58δ. The 4',4'a-isomer is also found in this peak as evidenced by a broad singlet at 4.61δ.

Peak B is identified as containing 4',4'a-dehydro-α-tocopherol and one of the trans isomers 3',4'-dehydro-α-tocopherol or 4',5'-dehydro-α-tocopherol.

Peak C: Of the three isolated fractions of dehydrotocopherol, this is the purest. The NMR spectrum is in agreement with one of the trans-isomers exhibiting a singlet at 1.55 for the vinyl methyl. No extraneous signals were detected.

Peak C is identified as containing either trans-3',4'-dehydro-α-tocopherol or trans-4',5'-dehydro-α-tocopherol. The identity of a α-tocopherol obtained by this process was also proven by 250 MHz NMR. A pure sample was obtained by preparative GC as described above and its 250 MHz spectrum was compared with that of authentic d,l-α-tocopherol. Close examination revealed that the samples are identical.

PATENTABILITY CONSIDERATIONS—VITAMIN E REFERENCES

References for typical syntheses of α-tocopherol from phytol and isophytol have been set forth under the heading BACKGROUND OF THE INVENTION.

The closest prior art appears to be set forth in: (1) "Synthesis of Vitamin E", *Kirk-Othmer Encyclopedia*, Volume 21, pages 574 to 585, 2nd Edition 1970. The mixture of eight possible stereoisomers commonly synthesized from racemic isophytol and also known as dl-α-tocopherol, 2-DL,4'DL,8'DL-α-tocopherol, or 2-RS,4'RS,8'RS-α-tocopherol, are designated as all-rac-α-tocopherol. One of the closest analogs to the instant dehydro and didehydro α-tocopherols is α-5,7,8-trimethyl tocotrienol which contains three unsaturated bonds in the side chain.

The Chapter by H. Mayer and O. Isler, "Synthesis of Vitamin E", is particularly valuable in understanding and distinguishing the present invention:

(2) *Methods in Enzymology*, Vol. XVIII, Vitamins and Coenzymes, Part C (pp.241–348) McCormick, Donald B. & Wright L. D., Academic Press, 1971.

In particular please note the α-5,7,8-trimethyl tocotrienols set forth in Table II, page 244 of reference No. 2 above, together with the following citations:

(3) O. Isler, H. Mayer, J. Metzger, R. Ruegg, and P. Schudel, *Angew Chem.* 75, 1030 (1963)

(4) P. Schudel, H. Mayer, J. Metzger, R. Ruegg, and O. Isler, *Helv. Chem. Acta* 46, 2517 (1963)

α-5,7,8-trimethyl tocotrienol is known to occur naturally in palm kernel oil and in wheat bran and can be synthesized from geranyl linalool as indicated in FIG. 14, page 270 of the Mayer and Isler Chapter. The importance of the compounds and process of the instant invention can be more fully appreciated by considering the complexity of the multi-step procedure depicted in FIG. 14 of that article as discussed on page 271:

"The tocotrienols cannot be synthesized by the conventional methods discussed for the synthesis of tocopherols since under strongly acidic conditions cyclization of the unsaturated side chain is a serious side reaction, a feature readily detected by nuclear magnetic resonance spectroscopy."

The instant process utilizes the specific unsaturated $C_{20}$ olefins and the corresponding unsaturated phytyl and unsaturated isophytyl compounds shown on page 4 of the specification and produces directly in one step (as opposed to the 4-step process of FIG. 14 of the reference) α-5,7,8-trimethyl tocodienol and α-5,7,8-trimethyl tocoenol. These compounds, also generally referred to as dehydro and didehydro-α-tocopherols in this specification, are readily converted to α-tocopherol (Vitamin E) by customary hydrogenation. Thus the present process has overcome the serious side reaction (cyclization of the unsaturated side chain) and provides a one-step synthesis of the Vitamine E precursor. This invention is even further remarkable in that it also provides for the synthesis of such compounds from the unsaturated $C_{20}$ hydrocarbons (phytatriene and phytatetraene) having a total of 3 and 4 ethylenic (double bond) unsaturation, thus eliminating the additional steps required to product the phytols, isophytols and their derivatives (phytyl halide etc.).

It is to be noted the dehydrophytols and didehydrophytols of the present invention (and corresponding isophytols) differ from the tetraene alcohol (geranyl linalool) depicted in FIG. 14 of the above article in that the instant compounds possess one or two double bonds less than possessed by said geranyl linalool. Correspondingly the resultant dehydro- and didehydro-α-tocopherols possess no unsaturation at the 7'position (side chain). The instant compounds thus are different and distinct from those shown in the Isler et al and Schudel et al references cited above.

It is to be further noted that the terms dehydro and didehydro phytol (and isophytol) used in this invention do not possess acetylenic unsaturation and hence are not equivalent to the ethynyl carbinols which are described in the following patents as dehydroisophytol (3,7,11,15-tetramethylhexadec-1-yn-3-ol).

(5) Czech. Pat. No. 127,030 (C.A. 70 685685); French Pat. No. 1,460,512 (C.A. 67 100279Z);

(6) German Pat. No. 1,768,877 (C.A. 75 129972W);

(7) German Pat. No. 1,218,150 (C.A. 66 29501n); and (8) German Pat. No. 1,911,503 (C.A. 72 3013d). It is noted that all these citations refer specifically to alkynl carbinols.

Further it should be noted that the compound 3,4-dehydro-α-tocopherol (CXIII), shown in FIG. 15 of Reference 2 (having unsaturation at the heterocyclic ring) is different from the 3',4'-dehydrotocopherols of the instant invention which have specific unsaturation in the $C_{20}$ side chain.

Additional background references include:

(9) L. I. Smith, H. E. Ungnade, and W. W. Prichard, *Sei* 88, 37–38 (1938) (phytadiene)

(10) P. Karrer, H. Fritzsche, B. H. Ringier, and H. Salomon, *Helv. Chem. Acta.* 21, 520–525 (1938).

(11) K. E. Mason, P. L. Harris, R. S. Harris, and H. A. Mattill, "The Tocopherols", *The Vitamins*, Vol. 3, Acedemic Press, New York, 1954, Chapter 17.

What is claimed is:
1. Dehydro-α-tocopherol isomers selected from the group consisting of cis- and trans-3',4'-dehydro-α-tocopherol; cis- and trans-4',5'-dehydro-α-tocopherol; and 4',4'-dehydro-α-tocopherol.
2. 3',4'-dehydro-α-tocopherol.
3. 4',5'-dehydro-α-tocopherol.
4. 4',4'a-dehydro-α-tocopherol.
5. Didehydro-α-tocopherols selected from the group consisting of cis- and trans-3',4'-11',12'-didehydro-α-tocopherol; cis- and trans-4',5'-11',12'didehydro-α-tocopherol; and 4',4'a-11',12'-didehydro-α-tocopherol.
6. 3',4'-11',12'-didehydro-α-tocopherol.
7. 4',5'-11',12'-didehydro-α-tocopherol.
8. 4',4'a-11',12'-didehydro-α-tocopherol.

UNITED STATES PATENT AND TRADEMARK OFFICE
CERTIFICATE OF CORRECTION

PATENT NO. : 4,168,271
DATED : September 18, 1979
INVENTOR(S) : Carlos G. Cardenas and Zia Ud Din It is certified that error appears in the above-identified patent and that said Letters Patent are hereby corrected as shown below:

Col. 1, line 2, change "April 3, 1977" to read --April 13, 1977--; Col. 1, at about line 30, in the structural formula dots (indicating unsaturation) should be indicated at the bond locations 3',4'; 4',4a'; 4',9' and 11',12'; Col. 7, line 9, change "tandard" to read --standard--; Col. 7, line 42, change "chloromyreene" to read --chloromyrcene--.

Signed and Sealed this

Eighth Day of January 1980

[SEAL]

Attest:

SIDNEY A. DIAMOND

Attesting Officer

Commissioner of Patents and Trademarks